US012611420B2

(12) United States Patent
He et al.

(10) Patent No.: US 12,611,420 B2
(45) Date of Patent: Apr. 28, 2026

(54) USE OF BETA-GLUCAN EXTRACT IN THE IMMUNOPOTENTIATION OF AN AVIAN ANIMAL

(71) Applicant: LESAFFRE ET COMPAGNIE, Paris (FR)

(72) Inventors: Cheng He, Beijing (CN); Tianyuan Zhang, Beijing (CN); Tadele Kiros Gebreyohannes, Marcq-en-Baroeul (FR)

(73) Assignee: LESAFFRE ET COMPAGNIE, Paris (FR)

( * ) Notice: Subject to any disclaimer, the term of this patent is extended or adjusted under 35 U.S.C. 154(b) by 0 days.

(21) Appl. No.: 17/052,478

(22) PCT Filed: Apr. 30, 2019

(86) PCT No.: PCT/IB2019/053515
§ 371 (c)(1),
(2) Date: Nov. 2, 2020

(87) PCT Pub. No.: WO2019/211735
PCT Pub. Date: Nov. 7, 2019

(65) Prior Publication Data
US 2021/0236536 A1 Aug. 5, 2021

(30) Foreign Application Priority Data

May 3, 2018 (CN) .......................... 201810416516.2

(51) Int. Cl.
*A61K 39/29* (2006.01)
*A61K 31/716* (2006.01)
(Continued)

(52) U.S. Cl.
CPC .......... *A61K 31/716* (2013.01); *A61K 36/064* (2013.01); *A61K 39/17* (2013.01);
(Continued)

(58) Field of Classification Search
None
See application file for complete search history.

(56) References Cited

U.S. PATENT DOCUMENTS 5,914,113 A * 6/1999 Schrier .................. A61K 39/39
435/235.1
2009/0053221 A1 2/2009 Cheung et al.
2018/0161424 A1* 6/2018 Tian ..................... A61K 39/295

FOREIGN PATENT DOCUMENTS

CN 1108575 A 9/1995
EP 0 640 348 A1 3/1995
(Continued)

OTHER PUBLICATIONS

Balasubramaniam et al., "Evaluation of an inactivated vaccine for nephropathogenic infectious bronchitis virus," Vet. World 6(3): 134-138 (Year: 2013).*
(Continued)

*Primary Examiner* — M Franco G Salvoza
(74) *Attorney, Agent, or Firm* — Venable LLP; Keith G. Haddaway

(57) ABSTRACT

The present invention relates to use of β-glucan extracts in the immunopotentiation of an avian animal. Specifically, the present invention provides a kit, wherein the kit comprises (1) an immunopotentiator used for immunopotentiation of an avian animal, wherein the immunopotentiator comprises a β-glucan extract which is extracted from *Saccharomyces cerevisiae* cell wall; and (2) a virus vaccine. The present invention also provides use of a β-glucan extract which is extracted from *Saccharomyces cerevisiae* cell wall, in the preparation of a kit used for immunopotentiation of an avian animal and immunopotentiator. The present invention uses a β-glucan extract, which is extracted from *Saccharomyces cerevisiae* cell wall, for immunopotentiation of an avian animal, which can enhance lymphocyte proliferation
(Continued)

responses and T cell responses of vaccinated animals; decrease the viral load; reduce the morbidity or mortality; produce antibodies in advance; and increase antibody production; and/or restrict the spread of the virus.

6 Claims, 4 Drawing Sheets

(51) Int. Cl.

| | |
|---|---|
| *A61K 36/064* | (2006.01) |
| *A61K 39/17* | (2006.01) |
| *A61K 39/215* | (2006.01) |
| *A61K 39/00* | (2006.01) |

(52) U.S. Cl.
CPC .... *A61K 39/215* (2013.01); *A61K 2039/5254* (2013.01); *A61K 2039/552* (2013.01); *C12N 2760/18134* (2013.01); *C12N 2770/20034* (2013.01)

(56) References Cited

FOREIGN PATENT DOCUMENTS

| | | | |
|---|---|---|---|
| TW | 200 902 059 A | 1/2009 | |
| WO | WO-2004078203 A2 * | 9/2004 | ............. A61K 39/12 |

OTHER PUBLICATIONS

Merriam Webster et al., "Immunopotentiation" as found at https://www.merriam-webster.com/medical/immunopotentiation (Year: 2024).*
International Search Report dated Aug. 2, 2019 in corresponding International Application No. PCT/IB2019/053515.
Written Opinion dated Aug. 2, 2019 in corresponding International Application No. PCT/IB2019/053515.
Le et al., "The Adjuvant Effect of Sophy beta-Glucan to the Anitbody Response in Poultry Immunized by the Avian Influenza A H5N1 and H5N2 Vaccines", Journal of Microbiology and Biotechnology, Apr. 1, 2011, vol. 21, No. 4, pp. 405-411.
Lehne et al., "Oral administration of a new soluble branched beta-1,3-D-glucan is well tolerated and can lead to increased salivary concentrations of immunoglobulin A in healthy volunteers", Clinical and Expermimental Immunology, 2005, vol. 143, pp. 65-69.
Vojtek et al., "Effects of orally administered beta-1,3/1,6-glucan on vaccination responses and immunological parameters in dogs", Food and Agricultural Immunology, 2017, vol. 28, No. 6, pp. 993-1002.
Wang et al., "Sulfated glucan can improve the immune efficacy of Newcastle disease vaccine in chicken", International Journal of Biological Macromolecules, Sep. 2014, vol. 70, pp. 193-198.
Christensen, "Vaccine adjuvants: Why and how", Human Vaccines & Immunotherapeutics, (2016), vol. 12, No. 10, pp. 2709-2711.
Lee et al., "Recent Advances of Vaccine Adjuvants for Infectious Diseases", Immune Network, (Apr. 2015), vol. 15, No. 2, pp. 51-57.
Wang et al., "Better Adjuvants for Better Vaccines: Progress in Adjuvant Delivery Systems, Modifications, and Adjuvant-Antigen Codelivery", Vaccines, (2020), vol. 8, (20 pages).
Office Action issued in Chinese Patent Application No. 2018104165162 on Sep. 28, 2022.
Harnack et al., "Oral administration of a soluble 1-3, 1-6 beta-glucan during prophylactic survivin peptide vaccination diminishes growth of B cell lymphoma in mice", International Immunopharmacology, Oct. 1, 2019, vol. 9, No. 11, pp. 1298-1303.
Office Action issued in European Application No. 19 729 810.2 on Feb. 12, 2026.
Retrieved from the Internet: URL:https://www.albitalia.com/en/yeast-derivative/macrogard/.

* cited by examiner

USE OF BETA-GLUCAN EXTRACT IN THE IMMUNOPOTENTIATION OF AN AVIAN ANIMAL

This application is a National Stage Application under 35 U.S.C. § 371 PCT/IB2019/053515, filed Apr. 30, 2019, which claims the benefit of priority to Chinese Patent Application No. 2018104165162, filed May 3, 2018, which is herein incorporated by reference in its entirety.

TECHNICAL FIELD

The present invention relates to the field of immunology, in particular to the use of β-glucan, a component of yeast (*Saccharomyces cerevisiae*) cell wall, as an immunopotentiator in avian.

BACKGROUND ART

One of the successful examples of modern medicine is the development of vaccines against infectious viruses. However, vaccines are not always effective in inducing the right type of immune responses against a given pathogen. Killed vaccines and subunit vaccines require adjuvants to potentiate their immunogenicity. Alum (aluminum salt) is the most commonly used vaccine adjuvant both in humans and animals. However, concerns over neurotoxicity of alum and the local reactions of alum induces, particularly when administered intradermal, are challenging the century old belief that Alum is a safe adjuvant. Furthermore, Alum induces strong Th2-type (humoral) response and is effective against extracellular pathogens, but has very little capacity to induce strong Th1 (cell mediated) responses, which are very important in combating many intracellular pathogens. Another potent adjuvant in the market is the Freund's adjuvant which is a water-in-oil emulsion with or without killed mycobacterium known as CFA and IFA, respectively. The complete Freund's adjuvant is abounded due to the strong reactions and necrosis it induced at the injection site. Therefore, there is still a strong demand for safe, nontoxic and effective adjuvants that can induce strong humoral and cell-mediated immunity. In addition to this, any new adjuvant to be developed, whether it is natural or synthetic product, should be suitable to use with new vaccine platform technologies including subunit vaccines, and has to be safe to be administered via different routes of vaccination, including oral, mucosal and intradermal. To this end, the applicant has developed a unique natural product, β-1,3/1,6-glucan, extracted from yeast (*Saccharomyces cerevisiae*) cell wall that fulfils all these safety criterion of safe adjuvant.

β-glucan particles have cell surface receptors that can interact with receptors on immune cells such as macrophages and dendritic cells to induce strong immunity. Furthermore, some in vitro assays have shown that β-glucans are able to train the immune system for memory responses suggesting that they can serve as good vaccine adjuvants. In addition to this, the porous and hollow structure of the β-glucan particles may allow the encapsulation of vaccines making them not only a good adjuvant, but also a perfect vaccine delivery system for subunit and DNA vaccines. Despite all these reports showing that β-glucan are able to induce strong immune response and boost vaccine induced immunity, there is no clear evidence that shows the use of β-glucan as vaccine adjuvant in animal vaccination with special reference to the avian industry.

Therefore, the main objective of the present invention is to examine the immune boosting potential of the β-glucan particle based vaccination protocols in avian against viral infection for which available vaccines are less effective in protecting the animal from infection. β-glucans can be given as feed additives before or during vaccination, which is the most economical way administering adjuvants to livestock, particularly avian. β-glucans can be also conjugated with the vaccine and administered either orally or parenterally together with the vaccine.

SUMMARY OF THE INVENTION

In order to solve one or more of the above problems in the prior art, in the first aspect, the present invention provides a kit, wherein the kit comprises: (1) an immunopotentiator used for immunopotentiation of an avian animal, wherein the immunopotentiator comprises a β-glucan extract which is extracted from yeast (*Saccharomyces cerevisiae*) cell wall; and (2) a virus vaccine.

In the second aspect, the present invention provides a use of a β-glucan extract in the preparation of the kit according to the first aspect, wherein the β-glucan extract is extracted from yeast (*Saccharomyces cerevisiae*) cell wall.

In the third aspect, the present invention provides a use of a β-glucan extract in the preparation of an immunopotentiator used for immunopotentiation of an avian animal, wherein the β-glucan extract is extracted from yeast (*Saccharomyces cerevisiae*) cell wall.

The present invention has the following advantages:
(1) being able to enhance lymphocyte proliferation responses and T cell responses of vaccinated animals;
(2) being able to decrease the viral load of vaccinated animals, thereby alleviating the physical burden of the large-load virus on the vaccinated animals;
(3) being able to reduce the morbidity or mortality of the vaccinated animals;
(4) being able to make the vaccinated animals produce antibodies in advance;
(5) being able to increase antibody production of the vaccinated animals; and/or
(6) being able to restrict the spread of the virus.

DESCRIPTION OF THE DRAWINGS

In order to understand the present invention and to know how to implement the present invention in the practice, the preferred embodiments are described below by way of non-limiting example only and with reference to the accompanying drawings, in which.

DETAIL DESCRIPTION

Figure 1:
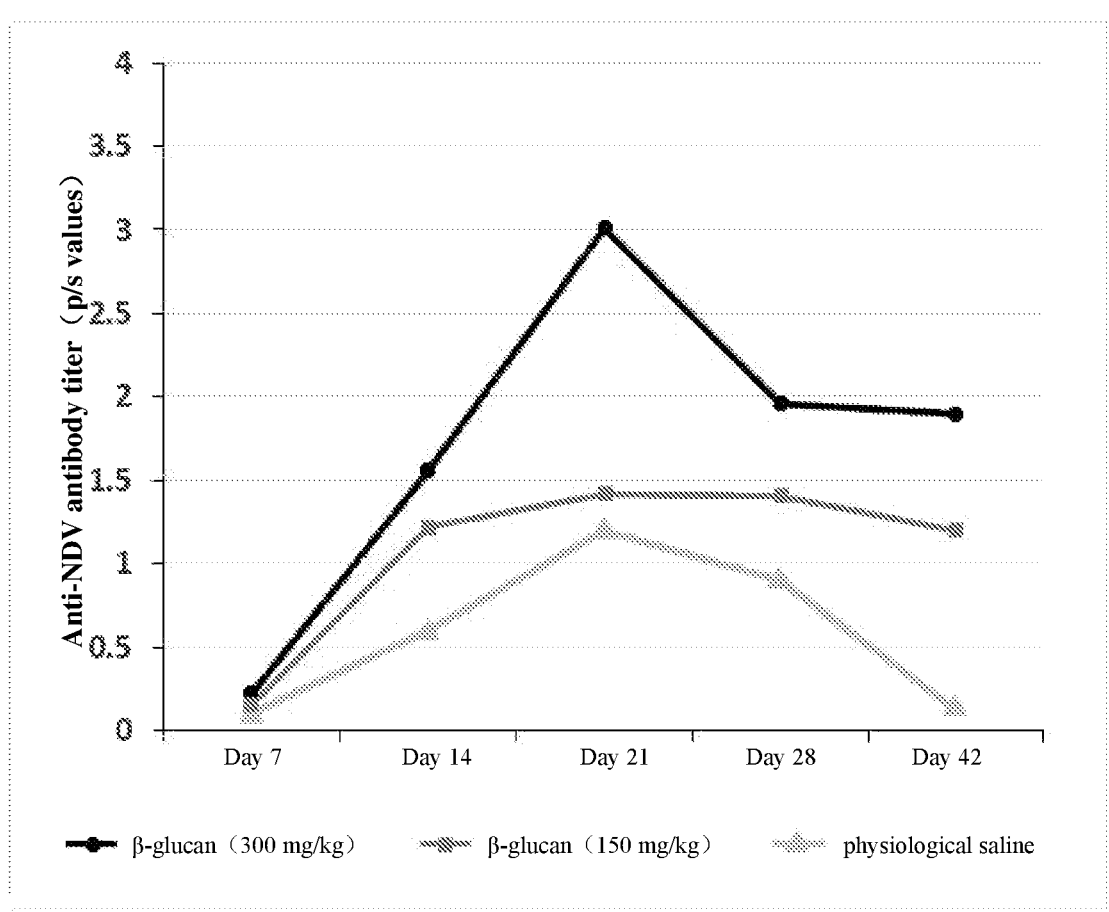
FIG. 1 shows anti-NDV antibody levels at different time points following vaccination with NDV vaccine in SPF (Specific Pathogen Free) chickens supplemented either with different doses of β-glucan orally in drinking water or control diet.

The present invention is further described below by way of specific embodiments. It is to be pointed out here that the following specific embodiments are merely used to illustrate the present invention, and those skilled in the art can improve the present invention according to the disclosure of the present invention in combination with the prior art under the premise of understanding the spirit and essence of the present invention. These technical solutions all fall within the scope of the present invention.

As mentioned above, in the first aspect, the present invention provides a kit, wherein the kit comprises (1) an immunopotentiator used for immunopotentiation of an avian animal, wherein the immunopotentiator comprises a β-glucan extract which is extracted from yeast (*Saccharomyces cerevisiae*) cell wall; and (2) a virus vaccine.

In some preferred embodiments, the virus vaccine is an inactivated virus vaccine or an attenuated vaccine. In other preferred embodiments, the virus vaccine can be selected from the group consisting of a DNA virus vaccine, a subunit vaccine, a Newcastle Disease virus (NDV) vaccine, and an infectious bronchitis virus (IBV) vaccine. In some more preferred embodiments, the virus vaccine is NDV vaccine and/or IBV vaccine.

In some preferred embodiments, the immunopotentiator comprises or consists of (1) β-1,3-glucan and β-1,6-glucan in a total amount of not less than 50% by weight; and/or (2) not more than 6% by weight of water. In other preferred embodiments, the immunopotentiator is in the form of sterile powder.

In some preferred embodiments, the β-glucan extract is rich in β-1,3-glucan and β-1,6-glucan, for example comprising β-1,3-glucan and β-1,6-glucan in a total amount of not less than 50% by weight. Additionally or alternatively, the water content of the β-glucan extract is not more than 6% by weight.

In some preferred embodiments, the immunopotentiator is a water-in-oil emulsion.

In some preferred embodiments, the immunopotentiator is an intramuscular injection formulation. One skilled in the art can determine the injected dose according to the teaching of this application. For example, the injected dose may be in the range of 100 mg/kg body weight to 500 mg/kg body weight, more preferably 150 mg/kg body weight to 300 mg/kg body weight, as calculated by β-glucan.

In some preferred embodiments, the immunopotentiator is an oral formulation or a feed additive. The present inventors have studied and found that the immunopotentiator of the present invention can be administered orally. For example, after immunization with a vaccine, the vaccinated animal can be allowed to drink water supplemented with the immunopotentiator. The ratio of the immunopotentiator and water may be set such that the concentration of the β-glucan therein is in the range of 1 wt % to 20 wt %, for example, 1 wt %, 2 wt %, 5 wt %, 10 wt %, 15 wt % or 20 wt %.

In the second aspect, the present invention provides use of a β-glucan extract in the preparation of the kit according to the first aspect of the present invention, wherein the β-glucan extract is extracted from yeast (*Saccharomyces cerevisiae*) cell wall.

In some preferred embodiments, the avian animal is an animal of Phasianidae, more preferably a Gallus animal, and further preferably a Red Jungle Fowl animal.

In some preferred embodiments, the immunopotentiator is used to (1) enhance lymphocyte proliferation responses and T cell responses of vaccinated animals; (2) decrease the viral load of vaccinated animals; (3) reduce the morbidity or mortality of vaccinated animals; (4) make vaccinated animals produce antibodies in advance; (5) increase antibody production of vaccinated animals; and/or (6) restrict the spread of the virus.

In some preferred embodiments, the viral vaccine and the immunopotentiator contained in the kit may be mixed or be each separately packaged.

In the third aspect, the present invention provides use of a β-glucan extract in the preparation of an immunopotentiator used for immunopotentiation of an avian animal, wherein the β-glucan extract is extracted from yeast (*Saccharomyces cerevisiae*) cell wall.

In some preferred embodiments, the immunopotentiator comprises or consists of (1) β-1,3-glucan and β-1,6-glucan in a total amount of not less than 50% by weight; and/or (2) not more than 6% by weight of water. In other preferred embodiments, the immunopotentiator is in the form of sterile powder.

In some preferred embodiments, the β-glucan extract is rich in β-1,3-glucan and β-1,6-glucan, for example comprising β-1,3-glucan and β-1,6-glucan in a total amount of not less than 50% by weight. Additionally or alternatively, the water content of the β-glucan extract is not more than 6% by weight.

In some preferred embodiments, the immunopotentiator is a water-in-oil emulsion.

In some preferred embodiments, the immunopotentiator is an intramuscular injection formulation. One skilled in the art can determine the injected dose according to the teaching of this application. For example, the injected dose may be 100 mg/kg body weight to 500 mg/kg body weight, more preferably 150 mg/kg body weight to 300 mg/kg body weight, as calculated by β-glucan.

In some preferred embodiments, the immunopotentiator is an oral formulation or a feed additive. The present inventors have studied and found that the immunopotentiator of the present invention can be administered orally. For example, after immunization with a vaccine, the vaccinated animal can be allowed to drink water supplemented with immunopotentiator. The ratio of the immunopotentiator and water may be set such that the concentration of the β-glucan therein is in the range of 1 wt % to 20 wt %, for example, 1 wt %, 2 wt %, 5 wt %, 10 wt %, 15 wt % or 20 wt %.

In some preferred embodiments, the animal is an avian animal. The animal is a Phasianidae animal, more preferably a Gallus animal, and further preferably a Red Jungle Fowl animal.

In some preferred embodiments, the kit is used to (1) enhance lymphocyte proliferation responses and T cell responses of vaccinated animals; (2) decrease the viral load of vaccinated animals; (3) reduce the morbidity or mortality of vaccinated animals; (4) make vaccinated animals produce antibodies in advance; (5) increase antibody production of vaccinated animals; and/or (6) restrict the spread of the virus. It is preferably that the animal is an avian animal.

The inventors adopted different vaccination routes to vaccinate SPF chickens with Newcastle Disease Virus (NDV) and Infectious Bronchitis Virus (IBV) vaccines. β-glucan particles were administered as an adjuvant during vaccination, and then different studies were conducted on SPF chickens to test the effect of the adjuvant. These studies included, for example: (1) 21-day-old SPF chickens were vaccinated with either NDV or IBV and supplemented orally in a drinking water with 300 mg/kg or 150 mg/kg β-glucan particles for 14 days; (2) β-glucan particles were injected intramuscular at a dose of 20 mg/kg or 10 mg/kg on the vaccination day with a second dose given 7 days later; (3) β-glucan particles were blended at 1% or 2% concentration with the inactivated NDV or IBV antigens and then emulsified with mineral oil into water-in-oil form vaccines, body weight gain and immune organ index (bursa fabricius, spleen, and thymus) were measured every week, and blood samples were also collected from the wing vein to determine antibody titers at different time points starting on day 7 post vaccination; and (4) lymphocyte proliferation assay was also conducted to measure cell-mediated immunity levels induced on day 7, day 14, and day 21 after vaccination. Different studies have shown that during vaccination of SPF chickens against viral diseases, administration of β-1,3/1,6-glucan can enhance cell-mediated virus-specific antibody response in vaccinated SPF chickens, which can increase the survival of SPF chickens and reduce the ability of the virus to spread after immunization with lethal doses of infectious virus particles.

Hereinafter, the present invention will be further described by way of examples. However, these examples are for illustrative purposes only and the protection scope of the present invention is not limited to these examples.

EXAMPLE

Materials

SPF chicken and chicken embryo: 580 21-day-old SPF chickens and 700 10-day-old chick embryos were purchased from Beijing Vital Bridge Experimental Animal Co. Ltd.

Feed: Purchased from a local commercial feed company.

Vaccine: Newcastle disease virus (NDV) and infectious bronchitis virus (IBV) attenuated vaccines were commercially available from Beijing Ceva-Huadou Biological Co. Ltd.

Medicament: β-glucan-containing yeast glucan was derived from Saccharomyces cerevisiae.

Test kit: ELISA kits for detection of antibodies against Newcastle disease virus (NDV) and infectious bronchitis virus (IBV) were purchased from IDEXX (Beijing) Co., Ltd.

New vaccine preparation: Firstly, the glucan from Saccharomyces cerevisiae (containing no less than 50% by weight of β-1,3-glucan and β-1,6-glucan, and not higher than 6 wt % of water) was dissolved in the form of an aqueous phase, and the NDV or IBV attenuated vaccine was then mixed with the yeast extract described above such that the concentration of β-glucan therein was 1 wt %, 2 wt %, 5 wt %, 10 wt % and 20 wt %, respectively. After preparation, new vaccines were stored at 4° C. for further detection.

Methods

Evaluation of Yeast Extracts in SPF Chickens:

Grouping: 80 21-day-old SPF chickens were divided into 4 groups, 20 SPF chickens for each group. The effect on SPF chickens of β-glucan from Saccharomyces cerevisiae cell wall provided by drinking water at doses of 300 mg/kg and 150 mg/kg was studied, and physiological saline and the vaccine administered alone were used as controls.

Immunization: After the animal had adapted to the environment, a dose of anti-NDV or IBV (0.05 ml per chicken) attenuated vaccine was administered by injection to the pectoralis of SPF chicken. After inoculation with the attenuated vaccine, β-glucan from Saccharomyces cerevisiae cell wall mentioned above was administered to SPF chicken by pectoral muscle injection.

Humoral Response:

The last day before immunization was set to day 0 (pre-immunization), and blood samples were collected from the wing vein of each group of 10 SPF chickens on day 7, day 14, day 21, day 28, and day 42. Anti-NDV and anti-IBV antibodies in chicken serum were detected using an ELISA kit.

Preparation of Inactivated Vaccine:

The new vaccine was diluted with physiological saline and then inoculated into 10-day old chicken embryos, 0.1 ml per chicken embryo. After inoculation, mortality was monitored daily. The inactivated NDV vaccine purchased from Beijing Ceva-Huadou Biological Co. Ltd. was inoculated into 10-day-old chicken embryos to determine the EID50. An inactivated NDV vaccine containing β-glucan from Saccharomyces cerevisiae cell wall was prepared under the standards and regulations of Chinese Pharmacopoeia (2010 edition). Firstly, NDV strains were collected from the allantoic cavity of SPF embryos and then inactivated by formalin according to the scheme described in Chinese Pharmacopoeia (2010 edition). Then, β-glucan was dissolved in the form of aqueous phase, and then the NDV antigen was mixed with the above-mentioned β-glucan so that the concentration of β-glucan therein was 1%, 2%, 5%, and 10% and 20%, respectively. After thorough mixing and testing, the formulation was aseptically filled into 10 ml and 20 ml containers. The final vaccine was stored at 4° C. for further use.

SPF Chicken Test:

10 SPF chickens were given a 0.05 ml dilution alone by eye drops, and 10 chickens were inoculated with physiological saline by pectoral muscle injection were used as a control. Finally, the vaccinated SPF chickens were monitored daily and observed for 14 days.

Efficacy Test:

(1) NDV antibody detection aNDV immune protection test: 70 SPF chickens were inoculated with NDV vaccine, 10 chickens in each group, and 10 chickens intranasally administered with 0.1 ml physiological saline were used as a control. On the 14th day after immunization, blood samples were collected to detect NDV antibody level with an ELISA kit, and then all SPF chickens were intramuscularly injected with 1.0 ml of a lethal Beijing strain ($1 \times 10^5$ ELD50/ml), and mortality was observed daily. The scheme was recorded on page 222 of Chinese Pharmacopoeia (2010 edition).

(2) IBV antibody test aNDV immune protection test: 70 SPF chickens were inoculated with IBV vaccine, 10 chickens in each group, and 10 chickens intranasally administered with 0.1 ml physiological saline were used as a control. On the 14th day after immunization, blood samples were collected to detect IBV antibody levels with an ELISA kit. All chickens were challenged intranasally with 2 drops of lethal M41 strain. After the challenging, more than 8 chickens obtained the protection. The scheme was recorded on page 214 of Chinese Pharmacopoeia (2010 edition).

Antibody Persistence after Immunization:

On the basis of efficacy tests, vaccine preparations were prepared according to page 224 of Chinese Pharmacopoeia (2010 Edition). 120 21-day-old SPF chickens were inoculated with each group of fresh vaccines, 10 chickens in each group. Blood samples were collected on day 14, day 30, day 60, and day 90 after inoculation, and then anti-NDV and IBV antibody levels were determined by ELISA kits.

Immunopotency Test:

SPF chickens were challenged through chest muscle injection with a lethal dose ($1 \times 10^5$ ELD50/ml). On the 14th day after the challenging (at this moment all the control groups died), the mortality was calculated. The calculation of mortality was based on the following criteria: (1) protection: SPF chickens showed a transient droop after infection, recovered after lassitude, and were able to self-collect food and drink water, without neurological symptoms or neck rotation phenomenon; (2) no protection: there were two cases: sick and death, the sick referred to limb tremor, circling and uncoordinated movement, lassitude, loss of appetite and water drinking, dropping down when get worse; and the death meant that the SPF chickens suffered from illness after challenging, and finally died. In the determination of viral load, the viral load of NDV was performed using glandular stomach, and the viral load of IBV virus was performed using trachea.

Statistical Analysis:

Data were expressed as average value±SEM (standard error of the average value). Student's T test was used for analysis. Differences were considered as significantly different when p<0.05, and differences were considered as highly significant different when p<0.01.

Results and Analysis

FIG. 1 shows anti-NDV antibody levels at different time points following vaccination with NDV vaccine in SPF chickens supplemented either with different doses of β-glucan orally in drinking water or control diet. As can be seen from FIG. 1, after immunization with NDV vaccine and different concentrations of β-glucan, the anti-NDV antibody titer of vaccinated chickens was significantly higher than that of the physiological saline control. Moreover, 300 mg/kg dose of β-glucan can obtain anti-NDV antibody titers significantly higher than that of 150 mg/kg dose of β-glucan, and were significantly higher from the beginning of immunization to day 42. In addition, for the immunopotentiation of 150 mg/kg dose of β-glucan, the peak of anti-NDV antibody titers occurred on day 21.

Figure 2:
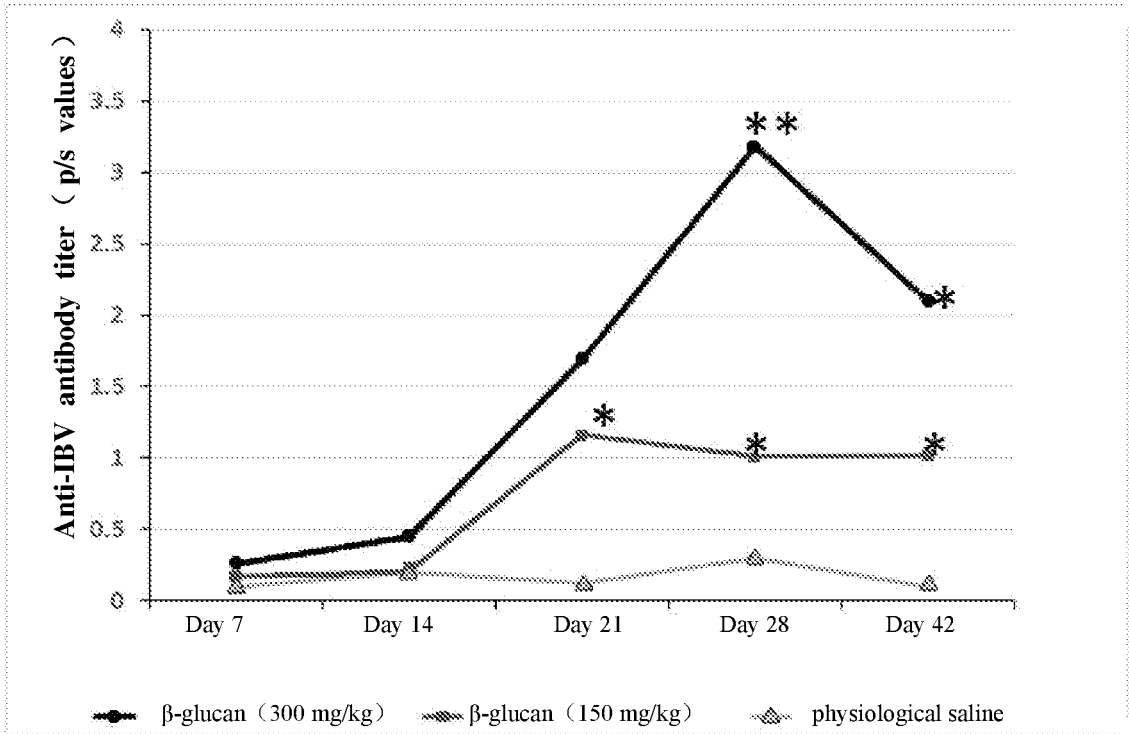
FIG. 2 shows anti-infectious bronchitis virus (IBV) antibody production following vaccination with IBV vaccine in SPF chicken fed with either different doses of β-glucan in drinking water or physiological saline for 14 days during vaccination.

FIG. 2 shows anti-infectious bronchitis virus (IBV) antibody production following vaccination with IBV vaccine in SPF chicken fed with either different doses of β-glucan in drinking water or physiological saline for 14 days during vaccination. As can be seen from FIG. 2, through immunizing with the IBV vaccine and immunopotentiation with β-glucan, the anti-IBV antibody titer, whether at a dose of 300 mg/kg or 150 mg/kg, was significantly higher than that of the physiological saline control. Moreover, 300-mg/kg dose of β-glucan can obtain anti-NDV antibody titers significantly higher than that of 150 mg/kg dose of β-glucan, and were significantly higher from the beginning of immunization to day 42. In addition, for the immunopotentiation of 150 mg/kg dose of β-glucan, the peak of anti-NDV antibody titers occurred on day 28.

Figure 3:
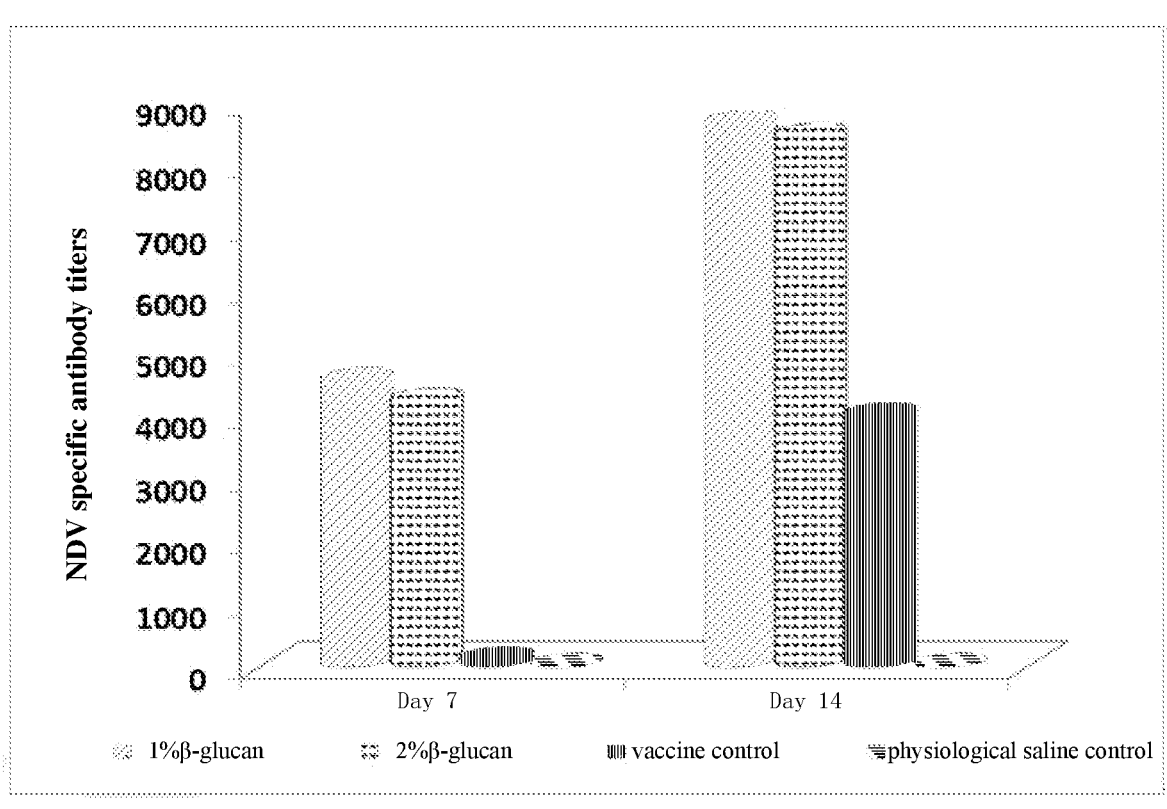
FIG. 3 shows the anti-NDV antibody titers on day 7 and day 14 post vaccination either in the presence of different concentrations of β-glucan as an adjuvant or vaccine only. Unvaccinated SPF chickens are used as negative controls.

FIG. 3 shows the anti-NDV antibody titers on day 7 and day 14 post vaccination either in the presence of different concentrations of β-glucan as an adjuvant or vaccine only. Unvaccinated SPF chickens were used as negative controls. As can be seen from FIG. 3, no antibody appeared on day 7 in the case of making no use of β-glucan, and antibody was produced on day 14. Under the circumstance of using 1% and 2% of β-glucan, antibody was produced on day 7 and an antibody level without using β-glucan was achieved. On day 14, the antibody production was almostly doubled.

Figure 4:
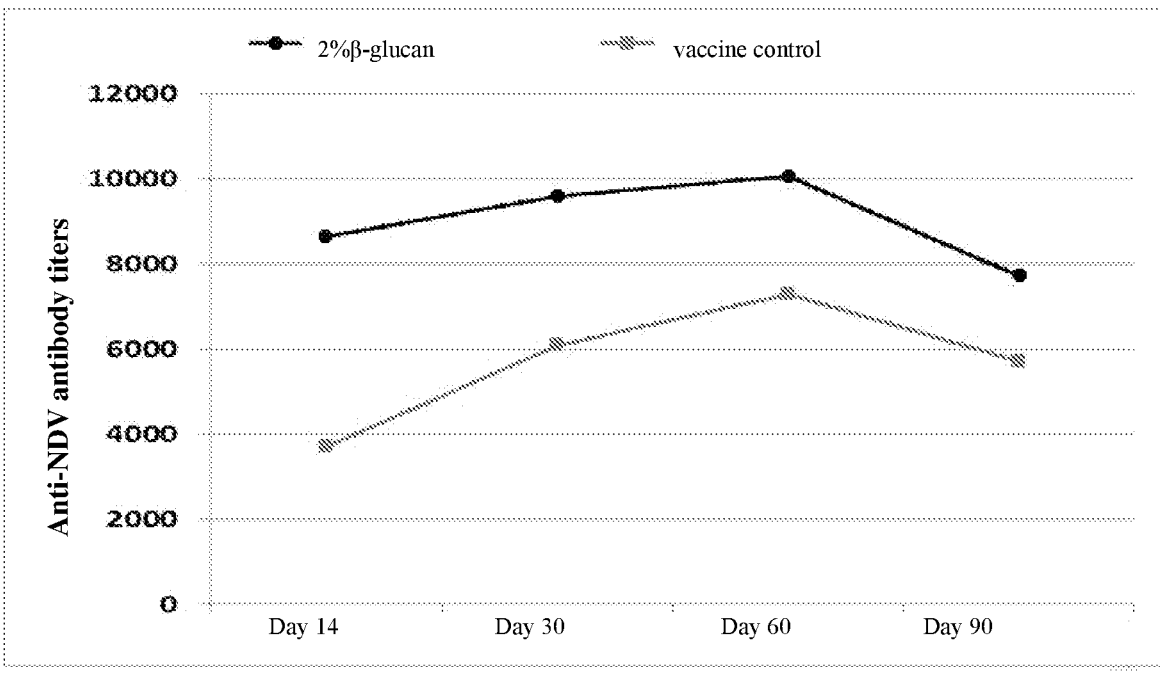
FIG. 4 shows the kinetics of anti-NDV antibody production over 90 days post vaccination in SPF chickens vaccinated with NDV vaccine in the presence or absence of 2% β-glucan as an adjuvant.

FIG. 4 shows the kinetics of anti-NDV antibody production over 90 days post vaccination of NDV in SPF chickens in the presence or absence of 2% β-glucan as an adjuvant. As can be seen from FIG. 4, when using 2% of β-glucan as an adjuvant, from day 14 to day 90 after immunization, NDV antibody titers were consistently significantly higher than those obtained without using 2% of β-glucan as an adjuvant.

Figure 5:
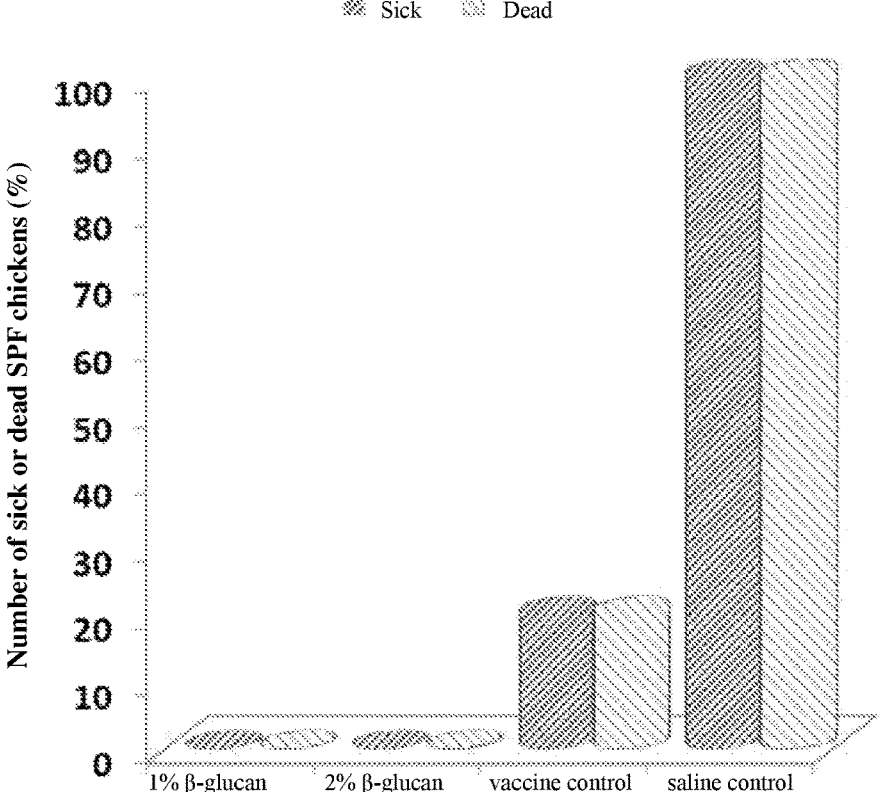
FIG. 5 shows the number of sick and dead SPF chickens following challenge of vaccinated SPF chickens with lethal dose of NDV. Vaccines were given either with different concentrations of β-glucan as adjuvant or physiological saline. Non vaccinated SPF chickens were used as negative controls.

FIG. 5 shows the number of sick and dead SPF chickens following challenge of vaccinated SPF chickens with lethal dose of NDV. Vaccines were given either with different concentrations of β-glucan as adjuvant or physiological saline. Non-vaccinated SPF chickens were used as negative controls. As can be seen from FIG. 5, strengthening the IBV vaccine by the use of β-glucan as an adjuvant can significantly reduce the morbidity and mortality of SPF chickens.

Figure 6:
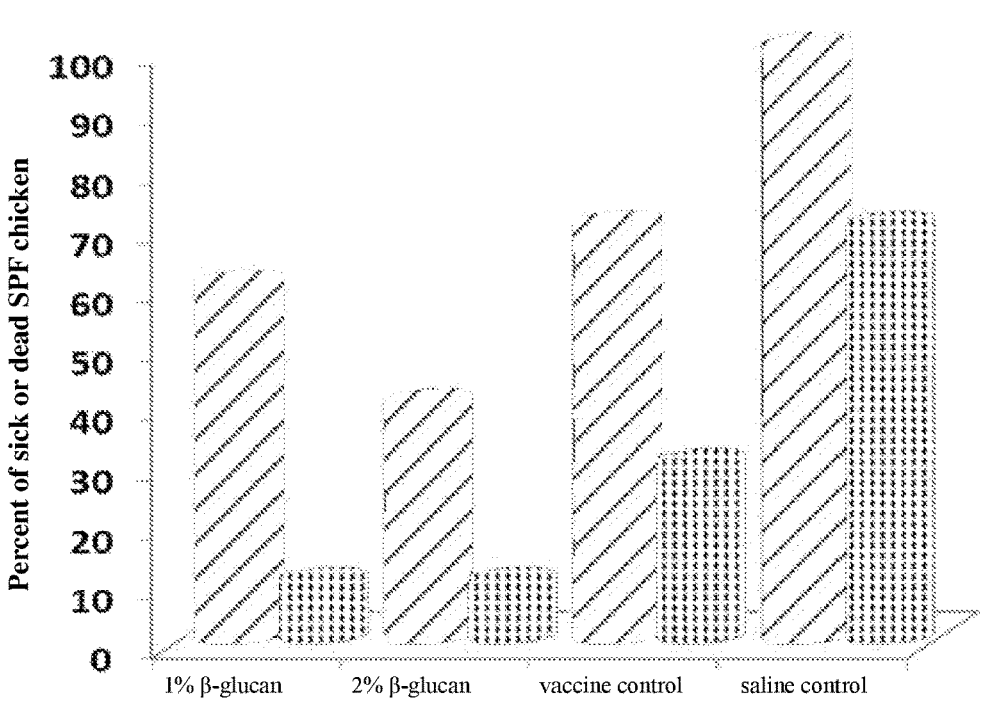
FIG. 6 shows the number of sick and dead SPF chickens following challenge of vaccinated SPF chickens with lethal dose of IBV. SPF chickens were vaccinated either in the presence of different concentrations of β-glucan as an adjuvant or physiological saline. Unvaccinated SPF chickens were used as negative controls.

FIG. 6 shows the number of sick and dead SPF chickens following challenge of vaccinated SPF chickens with lethal dose of IBV. SPF chickens were vaccinated either in the presence of different concentrations of β-glucan as an adjuvant or physiological saline. Unvaccinated SPF chickens were used as negative controls. As can be seen from FIG. 6, strengthening the IBV vaccine by the use of β-glucan as an adjuvant can significantly reduce the morbidity and mortality of SPF chickens.

Figure 7:
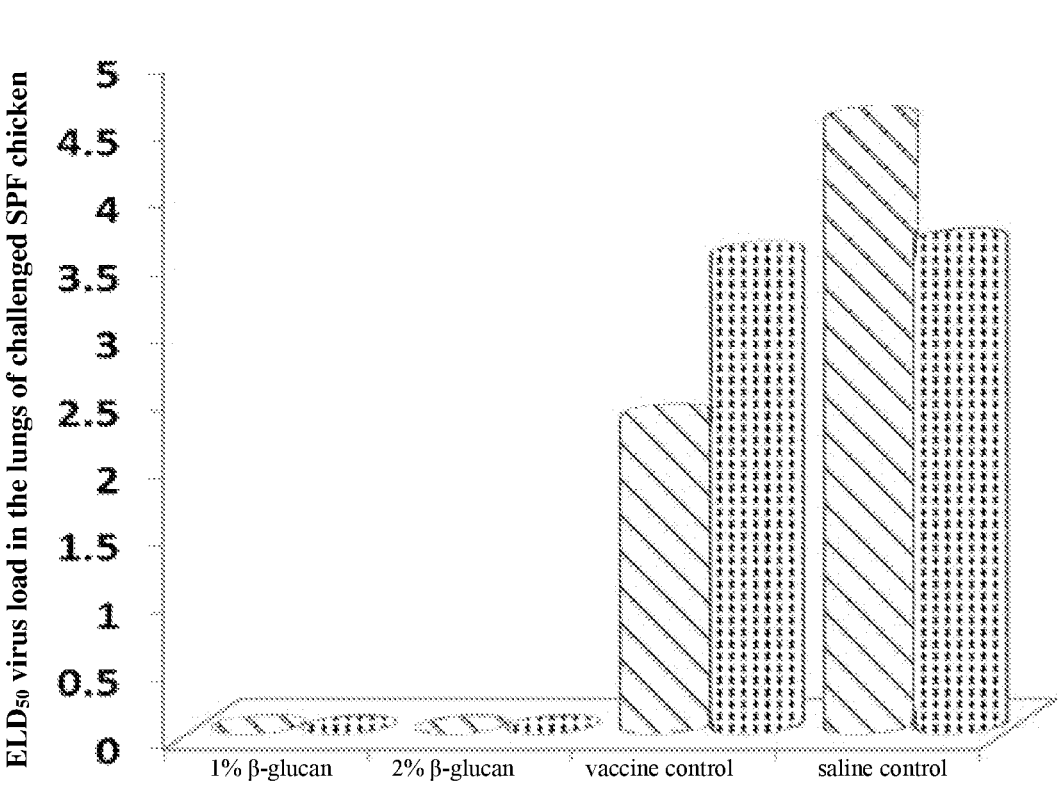
FIG. 7 shows virus shedding by SPF chickens either in the presence of different doses of β-glucan or physiological saline as adjuvant following challenge of SPF chickens with lethal doses of NDV or IBV. Unvaccinated SPF chickens were used as negative controls.

FIG. 7 shows virus shedding by SPF chickens either in the presence of different doses of β-glucan or physiological saline as adjuvant following challenge of SPF chickens with lethal doses of NDV or IBV. Unvaccinated SPF chickens were used as negative controls. As can be seen from FIG. 7, the amount of EID50 virus in the lungs of SPF chickens was almost 0 when using β-glucan as an adjuvant, regardless of NDV or IBV. Without using β-glucan as an adjuvant, regardless of a vaccine control or a saline control, there was a large amount of virus.

Although the present invention has been described in detail using general descriptions, embodiments, and tests, it can be modified or improved on the basis of the present invention, which will be obvious to those skilled in the art. Therefore, the modifications or improvements made without departing from the spirit of the present invention all fall within the protection scope of the present invention.

The invention claimed is:

1. A kit comprising:

(1) an immunopotentiator, wherein the immunopotentiator comprises a β-glucan extract which is extracted from *Saccharomyces cerevisiae* cell wall;

(2) an infectious bronchitis virus vaccine, and (3) water, wherein the immunopotentiator comprises β-1,3-glucan and β-1,6-glucan in a total amount of not less than 50% by weight;

wherein the ratio of the immunopotentiator to water is in the range of 1:99 to 20:80 by weight;

wherein the virus vaccine is an inactivated virus vaccine or an attenuated virus vaccine;

wherein the immunopotentiator, when administered to an avian animal in 150 mg of β-glucan per kg body weight of the avian animal to 300 mg of β-glucan per kg body weight of the avian animal, is effective to provide immunopotentiation against the infectious bronchitis virus.

2. The kit according to claim 1, wherein the immunopotentiator is a water-in-oil emulsion.

3. The kit according to claim 1, wherein the immunopotentiator is formulated for administration by intramuscular injection.

4. The kit according to claim 1, wherein the immunopotentiator is formulated for oral administration or as a feed additive.

5. The kit according to claim 1, wherein the immunopotentiation is at least one property chosen from:

(1) enhanced lymphocyte proliferation response and T cell response in the avian animal;

(2) decreased infectious bronchitis viral load in the avian animal;

(3) reduced morbidity or mortality in the avian animal;

(4) make vaccinated avian animals with an infectious bronchitis virus vaccine according to claim 1 produce antibodies;

(5) increased antibody production in the avian animal; and (6) decreased spread of the infectious bronchitis virus.

6. The kit according to claim 1, wherein the immunopotentiator comprises not more than 6% by weight of water.

* * * * *